(12) United States Patent
Cooper

(10) Patent No.: US 8,921,060 B2
(45) Date of Patent: Dec. 30, 2014

(54) HEALTH-BENEFICIAL PREPARATION AND PRODUCTION METHOD

(75) Inventor: Bryan Cooper, Mannheim (DE)

(73) Assignee: BASF SE (DE)

( * ) Notice: Subject to any disclaimer, the term of this patent is extended or adjusted under 35 U.S.C. 154(b) by 0 days.

(21) Appl. No.: 13/508,881

(22) PCT Filed: Oct. 11, 2010

(86) PCT No.: PCT/EP2010/065180
§ 371 (c)(1),
(2), (4) Date: May 9, 2012

(87) PCT Pub. No.: WO2011/057872
PCT Pub. Date: May 19, 2011

(65) Prior Publication Data
US 2012/0230923 A1  Sep. 13, 2012

(30) Foreign Application Priority Data
Nov. 10, 2009  (EP) .................................... 09014070

(51) Int. Cl.
| | | |
|---|---|---|
| A61K 35/74 | (2006.01) | |
| C12N 1/20 | (2006.01) | |
| A61Q 11/00 | (2006.01) | |
| A61K 8/99 | (2006.01) | |
| A23L 1/30 | (2006.01) | |
| A23L 2/52 | (2006.01) | |

(52) U.S. Cl.
CPC ................. *A23L 1/3014* (2013.01); *C12N 1/20* (2013.01); *A61K 8/99* (2013.01); *A61K 35/74* (2013.01); *A61Q 11/00* (2013.01); *A23L 2/52* (2013.01); *Y10S 435/854* (2013.01); *Y10S 435/853* (2013.01); *Y10S 435/885* (2013.01)
USPC ....... 435/7.34; 435/139; 435/252.9; 435/854; 435/853; 435/885; 424/93.3; 424/93.45; 424/93.1; 426/34; 426/43

(58) Field of Classification Search
CPC ............ A61K 35/744; A61K 2300/00; A61K 35/747; A61K 35/741; A61K 35/74; A61K 35/66; A61K 35/00; A61K 8/99; A61K 39/092; A23L 1/3014; A61Q 11/00; C12P 7/56; C12P 1/04; C12N 1/00; C12N 15/746; C12N 1/20; C12N 11/02; C12Q 1/00; C12Q 1/025
USPC ............. 435/139, 7.34, 252.9, 854, 853, 885; 424/93.3, 93.45, 93.1; 426/34, 43
See application file for complete search history.

(56) References Cited

U.S. PATENT DOCUMENTS

| | | | |
|---|---|---|---|
| 6,330,811 B1 | 12/2001 | Arman | |
| 7,037,708 B1 * | 5/2006 | Runge et al. | 435/243 |
| 2008/0193427 A1 * | 8/2008 | Kaesler et al. | 424/93.45 |

FOREIGN PATENT DOCUMENTS

| | | |
|---|---|---|
| CN | 1330253 A | 1/2002 |
| CN | 101056972 A | 10/2007 |
| RU | 2261610 C1 | 10/2005 |
| WO | WO-01/25411 A1 | 4/2001 |
| WO | WO-01/95741 A1 | 12/2001 |
| WO | WO 2004069156 A2 * | 8/2004 |
| WO | WO-2006/027265 A1 | 3/2006 |
| WO | WO 2006027265 A1 * | 3/2006 |

OTHER PUBLICATIONS

Langrish et al. 2001 (Spray drying of food ingredients and applications of CFD in spray drying, Chemical Engineering and Processing, 40: 345-354).*
International Search Report for PCT/EP2010/065180 mailed Feb. 2, 2011.
Mortazavian, A.M., et al., "Combined effects of temperature-related variables on the viability of probiotic micro-organisms in yogurt", Australian Journal of Dairy Technology, vol. 61, No. 3, (2006) pp. 248-252.
International Preliminary Report on Patentability PCT/EP2010/065180; Filing Date Oct. 11, 2010.

* cited by examiner

*Primary Examiner* — Ja'Na Hines
*Assistant Examiner* — Mary Lyons
(74) *Attorney, Agent, or Firm* — Drinker Biddle & Reath LLP

(57) ABSTRACT

The invention relates to the area of health-beneficial preparations and production methods thereof, in particular to the use of thermally pre-treated *Lactobacillus* preparations having specific bonding capacity for *Streptococcus mutans* for caries prophylaxis. The invention further relates to the *Lactobacillus* preparations and thermal pasteurization.

13 Claims, No Drawings

US 8,921,060 B2

HEALTH-BENEFICIAL PREPARATION AND PRODUCTION METHOD

RELATED APPLICATIONS

This application is a national stage application (under 35 U.S.C. §371) of PCT/EP2010/065180, filed Oct. 11, 2010 which claims benefit of European Application No. 09014070.8, filed Nov. 10, 2009.

FIELD OF THE INVENTION

The invention relates to the field of health-promoting products and preparation methods thereof.

BACKGROUND OF THE INVENTION

*Streptococcus mutans* plays a pivotal role in the development of caries. The bacterium converts fermentable sugars into organic acids and thus generates an acidic microenvironment. The organic acids are capable of demineralizing the dental enamel and thus bring about, or promote, the cariotic lesions. Moreover, *S. mutans* generates a non-water-soluble glucan matrix. This glucan matrix supports the development and adhesion of plaque and the adhesion of *S. mutans* at the surface of the teeth. Furthermore, it has been shown that other bacteria, too, are frequently found in carotic lesions, but always together with *S. mutans*. Accordingly, *S. mutans* is currently considered to be necessary for the development of cariotic lesions.

There is a constant need for remedies with which the development of cariotic lesions can be prevented. In this context, the invention intends to indicate remedies with which it is possible to act on *S. mutans* in order to avoid, stop or slow down the development of cariotic lesions. The invention also intends to indicate preparation methods for such remedies.

In the past, an entire series of remedies have been tested for controlling cariotic lesions, in particular in order to avoid or at least delay the appearance thereof. A person skilled in the art is familiar in particular with traditional chemical remedies for controlling caries and caries-associated microorganisms, as they are used in toothpastes and/or mouthwashes and/or other dental care products. In addition, however, it has also been attempted to control caries-associated microorganisms by means of other microorganisms or their products, in particular it has been attempted to reduce their amounts on teeth or in the oral cavity, or otherwise to influence the cariogenicity. Such an approach is described for example in WO 2005/027265 A1. However, the disadvantage is that the use of live microorganisms in oral care products is frequently disliked by consumers or entirely banned by legislators. Moreover, live microorganisms may influence the taste and/or the appearance of a product containing them as the result of metabolites; this influence may not be desired for every product for controlling cariotic lesions. Furthermore, the use of live organisms in products designed for controlling cariotic lesions limits the shelf-life of said products.

It is therefore quite generally attempted in various technical fields to use metabolically inactive microorganisms, in particular lyophilized microorganisms, instead of live microorganisms. The problem here, however, is that such microorganisms may, under conditions which are suitable for them, return to the metabolically active state, for example when they get into an aqueous medium which suits them. Accordingly, the use of metabolically inactive microorganisms entails serious limitations of the possible composition of a product containing them.

It has therefore been attempted in quite different technical fields to prepare products with destroyed microorganisms instead of live or metabolically active microorganisms. Thus, for example, WO 01/95741 A1 shows a foodstuff for promoting the intestinal balance, the food product containing nonviable Lactobacilli. The Lactobacilli can be made nonviable by means of heat treatment, for example by means of pasteurization or sterilization. Said document, however, also mentions the risk of losing, as a result of the heat treatment, some health-promoting effects of microorganisms which can otherwise be achieved. While the document says that these health-promoting effects can be eliminated "selectively", the document does, in fact, not teach anything about how the loss of a desired health-promoting feature might be avoided during the heat treatment of microorganisms. In the light of said document, therefore, a person skilled in the art can neither predict nor speculate in a meaningful manner as to which health-promoting effects are lost as a result of a heat treatment of microorganisms and which are not. In particular, it cannot be predicted or estimated whether an anticariogenic effect is lost as a result of heat treatment.

It is therefore the object of the present invention to indicate remedies for controlling cariotic lesions, in particular remedies for avoiding or delaying the development of cariotic lesions. In particular, it is intended that the remedies are guaranteed to bring about the desired effect. It is intended that their preparation be simple and inexpensive and that, if possible, the above-described disadvantages be avoided or reduced to a minor extent.

SUMMARY OF THE INVENTION

According to the invention, therefore, there is indicated a method of producing a nonlive *Lactobacillus* preparation with specific binding ability for *Streptococcus mutans*, comprising the following steps:

i) warming a suspension of cells of a *Lactobacillus* or a mixture of Lactobacilli with specific binding ability to *Streptococcus mutans*, where the specific binding
   a) is resistant to heat treatment and/or
   b) is resistant to protease treatment and/or
   c) is calcium-dependent and/or
   d) takes place in a pH range of between 4.5 and 8.5 and/or
   e) takes place in the presence of saliva,
from a starting temperature of below 40° C. to a pasteurization temperature of 75 to 85° C. with a temperature change of 0.5 to 2° C./min, ii) holding the warm suspension at the pasteurization temperature over a period of from 20 to 40 min, iii) cooling the suspension held in step ii) to a final temperature of below 40° C., with a temperature change of 0.5 to 2° C./min.

Such Lactobacilli are disclosed in WO 2006/027265 A1, which is herein incorporated by reference in its entirety for the purposes of the disclosure of the present invention.

DETAILED DESCRIPTION OF THE INVENTION

Surprisingly, it has emerged that a preparation which is entirely or essentially free from live, metabolically active Lactobacilli microorganisms while still having a specific binding ability for *Streptococcus mutans* can successfully be prepared by the Lactobacilli selected in accordance with the invention by means of pasteurization under mild conditions as described in the steps of the method according to the invention. A preparation prepared in accordance with the invention is therefore suitable for exerting an anticariogenic effect and, accordingly, useful as a remedy for preventing and/or treating caries. The terms "caries" and "cariotic lesion" are used interchangeably within the scope of the present document and refer to a chronic infectious disease which is distinguished by the development of softened patches on or in a tooth and which progressively leads to the death of the tooth. Caries can be diagnosed by known methods; a person skilled in the art can for this purpose refer to, for example, the paper by Angmar-Mansson and ten Bosch, Adv. Dent. Res. 7 (1993), 70 to 79.

For the purposes of the present invention, the term "controlling caries" or "controlling cariotic lesions" includes the prophylaxis of caries. Therefore, persons whose oral cavity should be free from *S. mutans* can therefore also benefit from other compositions which are prepared in accordance with the invention in as far as these compositions bind randomly introduced *S. mutans* cells and in this manner facilitate the removal of the latter.

For the purposes of the present invention, the term "treatment of caries" also includes the administration of the compositions prepared in accordance with the invention to a patient suffering from caries for the purposes of reducing the amount of *S. mutans* cells and, if appropriate, for the complete elimination of *S. mutans* from the mouth, in particular from the entire oral cavity including the teeth and the interdental spaces.

As regards the ability to bind *S. mutans*, the microorganisms selected in accordance with the invention are highly heat-stable. This allows to maintain the health-promoting effect of binding to *S. mutans*, which has been described in WO 2006/027265 A1 for live *Lactobacillus* cells, even after the pasteurization according to the invention, as opposed to, say, losing it. This is particularly uncommon since it would have been expected in principle for microorganisms that a considerable amount of, for example, their proteins would be denatured and other cell constituents dissolved or damaged upon pasteurization so that health-promoting effects of microorganisms are usually lost after pasteurization. Indeed, the abovementioned WO 01/95741 A1 merely shows that it is possible for certain Lactobacilli to maintain a health-promoting effect on the gut flora despite pasteurization. However, in terms of structure, content and use, the oral cavity is entirely different to the gut, so that a person skilled in the art could not have applied the findings of the last-mentioned documents to the present invention.

In accordance with a further aspect of the invention, accordingly, there is indicated a *Lactobacillus* composition with specific binding ability for *Streptococcus mutans*, which composition is obtainable or obtained by a preparation process according to the invention. Such a composition realizes the above-described advantages of the preparation process according to the invention, in particular it is suitable for preparing an anticariogenic product for use in the human body.

The *Lactobacillus* cells are preferably selected from among cells of strains of *Lactobacillus paracasei, Lactobacillus rhamnosus* or a mixture of these. The preparation process according to the invention can thus be carried out with a suspension of a pure culture of a *Lactobacillus* strain, in particular a strain of *Lactobacillus paracasei* or *Lactobacillus rhamnosus*, but also with a mixture of two, three, four, five, six, seven or more strains. Especially preferred for the process according to the invention are the *Lactobacillus* species and strains specified in WO 2006/027265 A1, in particular those with one of the DSMZ numbers DSMZ 16667, DSMZ 16668, DSMZ 16669, DSMZ 16670, DSMZ 16671, DSMZ 16672 and DSMZ 16673, in each case deposited on 26 Aug. 2004 at the Deutsche Sammlung für Mikroorganismen und Zellkulturen, Mascheroder Weg 1b, Brunswick, Germany. In as far as *Lactobacillus* cells are mentioned within the scope of the present invention, this is at least preferably also understood as meaning cells of the just-mentioned strains and mixtures of two, three, four, five, six or seven of the abovementioned strains. A person skilled in the art understands that, instead of, or additionally to, cells of one of the abovementioned strains, it is also possible to employ a mutant or a derived cell line in the method according to the invention, the mutant or derived cell line having retained the ability of specifically binding to *S. mutans*.

The *Lactobacillus* cells preferably have a specific binding ability for *Streptococcus mutans* Serotype c (DSMZ 20523) and/or Serotype e (NCTC 10923) and/or Serotype F (NCTC 11060).

A mutant, in particular a mutant of one of the abovementioned *Lactobacillus* strains, has one or more permanently inheritable modifications, usually its nucleic acid(s). Such modifications usually also encompass point mutations such as transitions or transversions, but also deletions, insertions and additions of one or more bases of a nucleic acid, whereby the nucleic acid is modified and a gene expression and/or transcription and/or translation, or inactivation, of gene products which deviates from what is normal is caused. Mutations can occur spontaneously or else be triggered by the action of agents such as, for example, chemicals or irradiation. Methods of selecting and obtaining mutants and derived cell lines are described, for example, in Sambrook, "Molecular cloning, a laboratory manual", Cold Spring Harbor Laboratory, NY, (2001) and in Ausubel, "Current protocols in molecular biology", Green Publishing Associates and Wiley Interscience NY, (1989). The skilled worker can find further information in WO 2006/027265 A1.

For the purposes of the present invention, "specific binding" or "specific binding ability" means for *Streptococcus mutans* that the *Lactobacillus* cells used in accordance with the invention, or the cells which have been pasteurized in accordance with the invention, bind to *S. mutans*, but do not bind to most, or all of, the remaining microorganisms which usually occur in the oral cavity in substantial amounts. The microorganisms selected in accordance with the invention preferably do not bind to cells of *Streptococcus salivarius, Streptococcus salivarius thermophilus, Streptococcus oralis, Streptococcus mitis* and/or *Streptococcus sanguinis*. The *Lactobacillus* cells used in accordance with the invention especially preferably do not bind to *Streptococcus salivarius* ssp. *thermophilus* API 50 CH (Biomerieux, France), *Streptococcus oralis* DSMZ 20066, *Streptococcus oralis* DSMZ 20395, *Streptococcus oralis* DSMZ 20627, *Streptococcus mitis* DSMZ 12643 and/or *Streptococcus sanguinis* DSMZ 20667. It is likewise preferred when the *Lactobacillus* cells used in accordance with the invention do not bind to bacteria of genera other than *Streptococcus*, that is to say for example not to cells of the genus *Staphylococcus*. Especially preferably, they do not bind to *Staphylococcus epidermidis* DSMZ 1798 and/or *Staphylococcus epidermidis* DSMZ 20044. To test the binding ability, the skilled worker proceeds as described in WO 2006/027265 A1 by mixing the abovementioned bacteria with the Lactobacilli selected in accordance with the invention, or their remainders which have been pasteurized in accordance with the invention, in a volumetric ratio of 3:1 and observing any aggregation caused by *Lactobacillus*. A suitable method is described in the abovementioned WO specification in example 3.

Accordingly preferred is a method according to the invention in which cells of one or more of the preferred *Lactoba-*

*cillus* strains, in particular *L. paracasei* or *L. rhamnosus* and preferably one or more of strains DSMZ 16667, DSMZ 16668, DSMZ 16669, DSMZ 16670, DSMZ 16671, DSMZ 16672 and DSMZ 16673 and especially preferably at least DSM 16671 and/or one mutant or derived cell line as described above are, in a first step, warmed in a suspension from a starting temperature of below 40° C. to a pasteurization temperature of from 75 to 85° C. with a temperature change from 0.5 to 2° C., are held, in a second step, at the pasteurization temperature for 20 to 40 min (pasteurization time) and in which the suspension, in a subsequent third step, is cooled to a final temperature of below 40° C. with a temperature change of from 0.5 to 2° C.

The pasteurization temperature in step i) is preferably 78 to 80° C., especially preferably 80° C. With such pasteurization temperatures, a rapid and, accordingly, energy-saving, yet secure, destruction of the *Lactobacillus* cells selected in accordance with the invention is successfully effected while simultaneously losing little binding ability in comparison with a nonpasteurized culture of live *Lactobacillus* cells.

The pasteurization time is preferably 25 to 35 min and especially preferably 30 min. It has emerged that in particular with a pasteurization temperature of 78 to 80° C. (preferably 80° C.), a rapid destruction of the *Lactobacillus* cells selected in accordance with the invention combined with a minor loss of *S. mutans* binding ability is possible in comparison with a live culture of the *Lactobacillus* cells.

It is likewise preferred when the temperature change in step i) or iii) is 0.8 to 1.2° C. per min, preferably 1° C. per min. In this manner, the heating-up time up to reaching the pasteurization temperature can be kept advantageously short so that energy can be saved, without thereby risking the destruction of the *Lactobacillus* cells or having to accept a great loss of binding ability for *S. mutans*.

Especially preferred is also a method according to the invention in which cells of one or more of the preferred *Lactobacillus* strains, in particular *L. paracasei* or *L. rhamnosus* and preferably one or more of strains DSMZ 16667, DSMZ 16668, DSMZ 16669, DSMZ 16670, DSMZ 16671, DSMZ 16672 and DSMZ 16673 and especially preferably at least DSM 16671 and/or one mutant or derived cell line as described above are, in a first step, warmed in a suspension from a starting temperature of below 40° C. to a pasteurization temperature of from 78 to 80° C., preferably 80° C., with a temperature change from 0.8 to 1.2° C., preferably 1° C., are held, in a second step, at the pasteurization temperature for 25 to 35 min and preferably 30 min (pasteurization time) and in which the suspension, in a subsequent third step, is cooled to a final temperature of below 40° C. with a temperature change of from 0.8 to 1.2° C., preferably 1° C.

The cells pasteurized in accordance with the invention are preferably in a post-exponential growth phase. It is especially preferred to use, in step i) of the preparation method according to the invention, cells from a culture medium which initially had allowed exponential growth, in which, however, the glucose concentration has dropped to a value of not more than 1 mM glucose. Here, it is preferred to use cells whose glucose concentration has dropped to a value of not more than 1 mM glucose for not more than 1 h, since otherwise the ability, of specifically binding to *Streptococcus mutans*, of the product of the preparation method according to the invention, i.e. of the result of step iii), if appropriate of the wash step or the spray-drying as described hereinbelow begins to be lost.

The method according to the invention furthermore preferably comprises a wash step in which the suspension obtained in step (iii) is centrifuged in order to concentrate the pasteurized cells, the concentrated cells thus obtained are treated with water and recentrifuged in order to reconcentrate the cells. The concentrated cells obtained are present as a substance with a dry-matter content of 10 to 30% by weight of the substance, preferably from 18 to 22% by weight.

Especially preferred in accordance with the invention is such a method which, besides steps i) to iii) (in particular applied to one, or a mixture of two, three, four, five, six or seven, of the *Lactobacillus* strains DSM 16667, DSM 16668, DSM 16669, DSM 16670, DSM 16671, DSM 16672 and DSM 16673 or of a mutant or cell line described hereinabove or of a strain of *L. paracasei* or *L. rhamnosus*) and, if appropriate, washing, comprises the following steps:

iv) treating the suspension obtained in step iii), preferably washed, with a carrier for preparing a spray-drying mixture, the carrier being selected from among alkali metal sulfates and alkaline-earth metal sulfates, preferably sodium sulfate, potassium sulfate or calcium sulfate, and mixtures of two or more of these sulfates, the amount of carrier being chosen such that the dry-matter content of the spray-drying mixture amounts to 10 to 30% by weight, and v) spray-drying of the spray-drying mixture obtained in step iv).

Spray-drying exposes the material to be dried to very harsh conditions and in particular to temperatures of, for example, 70° C. to 200° C. It was not known even from the *Lactobacillus* cells selected in accordance with the invention if they withstand the harsh conditions which occur during spray-drying without a significant loss of specific binding ability for *S. mutans*. What is more, with high amounts in accordance with the invention of carrier in step iv), it would have been expected that the surface structures of *Lactobacillus*, which are responsible for further binding to *S. mutans*, would be denatured or otherwise damaged. Surprisingly, it has now emerged that spray-drying of the suspension obtained in step iii) under the selected conditions is possible without a substantial loss of binding ability for *S. mutans*.

Some advantages of the spray-drying method according to the invention and of the spray-dried composition according to the invention prepared thus are particularly worthy of attention: in contrast to simple pasteurization, the spray-drying according to the invention allows a non tacky or hygroscopic composition to be obtained. In this context, hygroscopic means that open storage over a period of 12 months at a temperature of 20° C. and a relative humidity of 60%, the weight of the composition increased by no more than 2%. The composition according to the invention prepared thus is therefore particularly suitable for processing in dry products; it will not adversely affect the properties of these products as a result of attracting water or of being especially tacky.

The preparation method according to the invention furthermore makes it possible to prepare a composition according to the invention which is free-flowing. Particulate, free-flowing compositions can be stored and processed with particular ease, and they can be incorporated into a very wide range of products while being able to be dosed very precisely. Compositions according to the invention obtained by the spray-drying method according to the invention can thus be incorporated into a much wider product spectrum on an economically important scale than the suspension obtained directly after step iii).

Especially preferred as the carrier in step iv) is sodium sulfate. The amount of carrier, especially preferably of sodium sulfate, preferably amounts to times the dry matter of the suspension employed from step iii). The spray-drying mixture employed for spray-drying in step v) will in this case contain approximately 20% by weight of total dry-matter.

Spray-drying is effected in step v), preferably at a gas inlet temperature of a spray-drying gas employed for drying of from 180 to 250° C. and a gas outlet temperature from the zone provided for drying, usually a spray tower, of from 70 to 100° C., preferably 85° C., the average residence time in the reaction zone of the spray-drying gas of the material to be dried being from 10 to 60 seconds, preferably from 20 to 40 seconds. A person skilled in the art can furthermore take guidance on spray-drying from the information provided in WO 01/25411 A1. This document describes generally suitable spray-drying methods for the preparation of spray-dried enzyme products. Surprisingly, it has now emerged that spray-drying without substantial loss of binding ability for *S. mutans* is possible even at the higher temperatures which are preferred in accordance with the invention. This could not have been expected on the basis of WO 01/25411 A1, in particular because said document does not describe a single example of a working spray-drying step following pasteurization and since a person skilled in the art would consider the document to be speculative as regards the suitability of spray-drying for an allegedly very wide class of enzymes.

Therefore, a method according to the invention which is especially preferred is one in which:

(i) cells of one or more of the preferred *Lactobacillus* strains, in particular *L. paracasei* or *L. rhamnosus* and preferably one or more of strains DSMZ 16667, DSMZ 16668, DSMZ 16669, DSMZ 16670, DSMZ 16671, DSMZ 16672 and DSMZ 16673 and especially preferably at least DSM 16671 and/or one mutant or derived cell line in a post-exponential growth phase as described above are, in a first step, warmed in a suspension from a starting temperature of below 40° C. to a pasteurization temperature of from 78 to 80° C., preferably 80° C., with a temperature change from 0.8 to 1.2° C., preferably 1° C., and, subsequently, (ii) the suspension is held for 25 to 35 min and preferably for 30 min at the pasteurization temperature, and, subsequently, (iii) the suspension is cooled to a final temperature of below 40° C. with a temperature change of 0.8 to 1.2° C., preferably 1° C., is subsequently washed with water as described above and brought to a dry-matter content of from 10 to 30% by weight, preferably from 18 to 22% by weight, by centrifugation, and, subsequently, (iv) the suspension is treated with a carrier for preparing a spray-drying mixture, the carrier being selected from among sodium sulfate, potassium sulfate and calcium sulfate and mixtures of two or more of these and especially preferably sodium sulfate, the amount of carrier being chosen such that the dry-matter content of the spray-drying mixture amounts to from 10 to 30% by weight, and, subsequently, (v) the carrier-containing suspension obtained in step (iv) is spray-dried at a gas inlet temperature of a spray-drying gas employed for drying of from 180 to 250° C. and a gas outlet temperature from the zone provided for drying, usually a spray tower, of from 70 to 100° C., preferably 85° C., the average residence time in the reaction zone of the spray-drying gas of the material to be dried being from 10 to 60 seconds, preferably from 20 to 40 seconds.

This method realizes the above-described advantages of the invention.

The *Lactobacillus* composition according to the invention with a specific binding ability for *Streptococcus mutans*, which composition is obtainable obtained by a method with steps i) to iii) and optionally iv) to v) is preferably incorporated into a product for use in the human body. When used for the human body, in particular by introducing into the oral cavity and/or by bringing into contact with teeth, it is indeed possible to carry out a caries prophylaxis using the compositions according to the invention.

The products according to the invention expediently comprise the composition according to the invention in an amount which suffices for binding to *S. mutans* and/or for obtaining an anticariogenic effect. This amount depends on the nature of the product in question and on its pharmaceutical presentation. In particular, the amount also depends on the specifically desired extent of the possible binding to *S. mutans* or of the possible anticariogenic effect. Depending on the product, a person skilled in the art will, by means of routine experiments, readily determine the amount of composition according to the invention which suffices with regard to the desired extent of the effect, the nature of the product and the pharmaceutical presentation. In particular, a person skilled in the art will take into consideration that a product can be coated with the composition according to the invention or can have this composition incorporated by admixing.

A product according to the invention is preferably selected from the group consisting of food products, including luxury food products, beverage products, semifinished products, oral hygiene products, cosmetic products and pharmaceutical products. Corresponding products are described in WO 2006/027265 A1.

Especially preferred products are chewing gum, toothpaste, oral rinses and lozenges.

The invention is hereinbelow described with reference to the examples, but the examples are not intended to limit the scope of protection of the claims.

Example 1

General Preparation Process

*Lactobacillus* cells with a specific binding ability to *Streptococcus mutans*, were the specific binding
a) is resistant to heat treatment and/or
b) is resistant to protease treatment and/or
c) is calcium-dependent and/or
d) takes place in a pH range of between 4.5 and 8.5 and/or
e) takes place in the presence of saliva, are cultured in a suitable aqueous nutrient medium at 37° C. A suitable nutrient medium contains glucose, yeast extract, Tween 80 and salts. Culturing is done as an aqueous suspension in a fed-batch operation.

As soon as the glucose content of the nutrient medium has dropped below 1 mM, or up to 1 hour after this point in time, the suspension is warmed to a pasteurization temperature of from 75 to 85° C., preferably from 78 to 80° C. In this context, the suspension is warmed with a temperature change of from 0.5 to 1.2° C./min, preferably from 0.8 to 1.2° C./min.

The warm suspension is held at the pasteurization temperature for 20 to 40 minutes, preferably 25 to 35 minutes and especially preferably 30 minutes.

The suspension is subsequently cooled to below 40° C. In this context, the temperature change amounts to from 0.5 to 2° C./min, preferably from 0.8 to 1.2° C./min.

The cool suspension subsequently concentrated to a dry-matter content of from 10 to 30% by weight by means of centrifugation. The concentrate thus obtained is resuspended in water and again concentrated to a dry-matter content of from 10 to 30% by weight by means of centrifugation. Resuspending and concentrating is carried out up to 8 times in total. At the end, a washed biomass with a dry-matter content of from 10 to 30% by weight is obtained.

This biomass still retains the ability of specifically binding to *Streptococcus mutans*, as described at the outset in the example. The biomass per se can be incorporated into foodstuffs, including luxury foodstuffs, beverages, semifinished products, oral hygiene products, cosmetic products or pharmaceutical products in order to equip the product for controlling caries or in order to support its already preexisting ability to control caries.

Example 2

Preparation of an Oral Care Composition

A culture of *L. paracasei* or *L. rhamnosus* with the specific binding ability to *Streptococcus mutans* which has been defined in accordance with the invention is cultured, pasteurized and washed as described in example 1. The pasteurization temperature is 0° C. The pasteurization time is 30 min. The temperature change is in each case from 0.8 to 1.2° C./min. The concentrated suspension obtained after the first centrifugation is resuspended to a dry-matter content of 5% by weight of the resuspension by adding water. The resuspension thus obtained is recentrifuged down to a dry-matter content of 20% by weight.

The washed and concentrated biomass thus obtained is treated with an aqueous carrier and flavorings. This gives an oral rinse for controlling caries.

In the same manner, washed and concentrated biomass prepared with DSMZ 16667, DSMZ 16668, DSMZ 16669, DSMZ 16670, DSMZ 16671, DSMZ 16672 or DSMZ 16673 is obtained. This biomass is in each case likewise treated with an aqueous carrier and with flavorings in order to obtain in each case an oral rinse for controlling caries.

Chewing gums, toothpastes and lozenges for controlling caries are produced instead of an oral rinse by incorporating the respective washed and concentrated biomass into chewing gum base, toothpaste base and lozenge base and adding desired flavorings.

Example 3

General Spray-Drying Method

A basic spray-drying solution is prepared by preparing an aqueous, 10 to 30% strength alkali and/or alkaline-earth sulfate solution. The washed and concentrated biomass obtained as described in example 1 is resuspended in the four-fold quantity of the basic spray-drying solution for forming a spray-drying mixture, so that 500 units of volume of spray-drying mixture are obtained from 100 units of volume of the biomass.

The spray-drying mixture is spray-dried by introducing into a spray-drying tower. The spray-drying tower is charged with a spray-drying gas, the spray-drying gas having an inlet temperature into the spray-drying tower of 180 to 250° C. and an outlet temperature from the spray-drying tower of from 70 to 100° C. The spray-drying mixture has a mean residence time in the spray-drying tower of not more than 60 seconds.

The spray-dried material obtained still retains the ability of specifically binding to *Streptococcus mutans* as described at the outset in example 1. The resulting spray-dried material per se can be incorporated into foodstuffs, including luxury foodstuffs, beverages, semifinished products, oral hygiene products, cosmetic products or pharmaceutical products in order to equip the product for controlling caries or in order to support its already preexisting ability to control caries.

Example 4

Preparation of a Further Oral Care Composition

A culture of *L. paracasei* or *L. rhamnosus* with the specific binding ability to *Streptococcus mutans* which has been defined in accordance with the invention is cultured, pasteurized and washed as described in example 1. The pasteurization temperature is 80° C. The pasteurization time is 30 min. The temperature change is in each case from 0.8 to 1.2° C./min. The concentrated suspension obtained after the first centrifugation is resuspended to a dry-matter content of 5% by weight of the resuspension by adding water. The resuspension thus obtained is recentrifuged down to a dry-matter content of 20% by weight.

The resuspension is subsequently spray-dried in a spray-drying method as described in example 3. The basic spray-drying solution is an aqueous 20% strength sodium sulfate solution. The inlet temperature of the spray-drying gas into the spray tower is 180-250° C. The outlet temperature of the spray-drying gas from the spray tower is 70-100° C. The mean residence time of the spray-drying mixture in the spray tower is 10 seconds.

This gives a spray-dried material. The spray-dried material is treated with an aqueous carrier and with flavorings. This gives an oral rinse for controlling caries.

In the same manner, spray-dried material is prepared with DSMZ 16667, DSMZ 16668, DSMZ 16669, DSMZ 16670, DSMZ 16671, DSMZ 16672 or DSMZ 16673. This material is likewise also treated with an aqueous carrier and with flavorings in order to obtain in each case an oral rinse for controlling caries.

Chewing gums, toothpastes and lozenges for controlling caries are produced instead of an oral rinse by incorporating the respective material into chewing gum base, toothpaste base and lozenge base and adding desired flavorings.

The invention claimed is:

1. A method for preparing a composition comprising non-live *Lactobacillus* with specific binding ability for *Streptococcus mutans*, comprising the following steps:
   i) warming a suspension of cells of a *Lactobacillus* or a mixture of Lactobacilli with specific binding ability to *Streptococcus mutans* from a starting temperature of below 40° C. to a pasteurization temperature of 75 to 85° C. with a temperature change of 0.5 to 2° C./min, where the specific binding
      a) is resistant to heat treatment;
      b) is resistant to protease treatment;
      c) is calcium-dependent;
      d) takes place in a pH range of between 4.5 and 8.5; and/or
      e) takes place in the presence of saliva,
   ii) holding the warm suspension at the pasteurization temperature over a period of 20 to 40 min,
   iii) cooling the suspension held in step ii) to a final temperature of below 40° C., with a temperature change of 0.5 to 2° C./min.

2. The method according to claim 1, wherein the *Lactobacillus* cells are selected from the group consisting of cells of strains of *Lactobacillus paracasei*, cells of strains of *Lactobacillus rhamnosus*, and a mixture thereof.

3. The method according to claim 1, wherein the *Lactobacillus* cells are selected from the group consisting of cells of *Lactobacillus paracasei*, and cells of *Lactobacillus rhamnosus*.

4. The method according to claim 1, wherein the *Lactobacillus* cells have a specific binding ability for *Streptococcus*

*mutans* Serotype c (DSMZ 20523), Serotype e (NCTC 10923), and/or Serotype F (NCTC 11060).

5. The method according to claim 1, wherein the pasteurization temperature in step i) is from 78 to 80° C.

6. The method according to claim 1, wherein the temperature change in step i) and/or iii) is from 0.8 to 1.2° C./min.

7. The method according to claim 1, wherein in step i) the suspension comprises not more than 10 mmol glucose/l.

8. The method according to claim 1, further comprising the following steps:
   iv) treating the suspension obtained in step iii) with a carrier to obtain a spray-drying mixture, the carrier being selected from the group consisting of alkali metal sulfates and alkaline-earth metal sulfates, wherein the amount of carrier is chosen such that the spray-drying mixture has a dry-matter content of 10 to 30% by weight and;
   v) spray-drying the spray-drying mixture obtained in step iv).

9. The method according to claim 8, wherein the spray-drying is effected at a gas inlet temperature of a spray-drying gas employed for drying of from 180 to 250° C., and a gas outlet temperature from a zone provided for drying of from 70 to 100° C., and the average residence time in the zone is from 10 to 60 seconds.

10. The method according to claim 1, wherein the *Lactobacillus* cells are selected from the group consisting of the deposited strains DSMZ 16667, DSMZ 16668, DSMZ 16669, DSMZ 16670, DSMZ 16671, DSMZ 16672 and DSMZ 16673.

11. The method according to claim 8, wherein the spray-drying is performed in a spray tower.

12. The method according to claim 8, wherein the gas outlet temperature is 85° C.

13. The method according to claim 8, wherein the average residence time in the zone is from 20 to 40 seconds.

* * * * *